United States Patent [19]
Chen et al.

[11] Patent Number: 6,020,515
[45] Date of Patent: Feb. 1, 2000

[54] PROCESS FOR THE PREPARATION OF MALONONITRILE

[75] Inventors: Peter Chen; Johannes Hoffner, both of Zürich; Andrë Mueller, Geroldswil; Rudolf Fuchs, Sion, all of Switzerland

[73] Assignee: Lonza, Ltd., Gampel/Valais, Switzerland

[21] Appl. No.: 09/272,394

[22] Filed: Mar. 19, 1999

[30] Foreign Application Priority Data

Mar. 19, 1998 [CH] Switzerland .............................. 0664/98

[51] Int. Cl.$^7$ ...................... C07C 253/00; C07C 255/00; C07C 249/00

[52] U.S. Cl. ............................ 558/314; 558/408; 558/446

[58] Field of Search ...................................... 558/314, 408, 558/446

[56] References Cited

PUBLICATIONS

Ullmann's Encyklopädie der Technischen Chemie, 4$^{th}$ Revised and Expanded Edition, Verlag Chemie Weinheim, vol. 16, pp. 419–423.

*Primary Examiner*—Johann Richter
*Assistant Examiner*—Joseph Murray
*Attorney, Agent, or Firm*—Fisher, Christen&Sabol

[57] ABSTRACT

A novel process for the preparation of malononitrile which involves subjecting a (2-cyano-N-alkoxy)acetimidoyl halide to a high-temperature treatment.

8 Claims, No Drawings

PROCESS FOR THE PREPARATION OF MALONONITRILE

BACKGROUND OF THE INVENTION

1. Field of the Invention

The invention relates to a novel process for the preparation of malononitrile.

2. Background of the Invention

Malononitrile is a starting material and intermediate of central importance for the preparation of an extremely wide range of, for example, pharmaceutical or agrochemical active ingredients (Ullmann's Encyklopadie der technischen Chemie, 4$^{th}$ revised and expanded edition, Verlag Chemie Weinheim, Volume 16, pp. 419–423).

Although a large number of processes are known for the preparation of malononitrile, the only one to have achieved significance on an industrial scale is the high-temperature reaction of acetonitrile with cyanogen chloride at temperatures above 700° C.

BROAD DESCRIPTION OF THE INVENTION

The object of the invention is to develop an alternative process with the potential for use on an industrial scale. The object of the invention is achieved by the process of the invention.

According to the invention, a (2-cyano-N-alkoxy) acetimidoyl halide of the general formula:

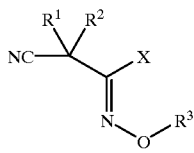

I in which $R^1$ and $R^2$ are identical or different and are hydrogen or alkyl, $R^3$ is alkyl, cycloalkyl, aryl, arylalkyl or a group:

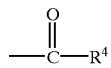

in which $R^4$ is an alkyl, aryl or arylalkyl group, and X is a halogen atom, is converted into malononitrile at a temperature of from 500° to 1000° C.

DETAILED DESCRIPTION OF THE INVENTION

Alkyl group is expediently taken to mean a $C_{1-6}$-alkyl group, namely, methyl, ethyl, n-propyl, isopropyl, n-butyl, isobutyl, t-butyl, pentyl and its isomers or hexyl and its isomers. A preferred meaning of $R^1$ is methyl.

Cycloalkyl is expediently a $C_{3-6}$-cycloalkyl group, namely, cyclopropyl, cyclobutyl, cyclopentyl or cyclohexyl.

Aryl is expediently optionally substituted phenyl or naphthyl, and arylalkyl is expediently a benzyl group. Both the alkyl and the aryl group can be provided with suitable substituents. Examples which may be mentioned are: $C_{1-4}$-akyl, $C_{1-4}$-alkoxy, $C_{1-4}$-alkanoyl, halogen, nitro, amino, alkylamino or dialkylamino.

Halogen has the meaning of fluorine, chlorine, bromine or iodine, preferably bromine or chlorine. The (2-cyano-N-alkoxy)acetimidoyl halides, as starting compound for the high-temperature treatment, can be expediently prepared by halogenation of a (2-cyano-N-alkoxy)acetamide of the general formula:

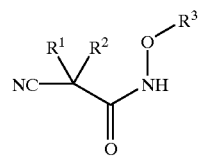

II in which $R^1$, $R^2$ and $R^3$ are as defined above.

The halogenation is preferably a chlorination and is carried out using suitable halogenating agents, such as, phosphorus pentachloride, phosgene, phosphorus oxychloride or tetrachloromethane in conjunction with triphenylphosphine.

The reaction is expediently carried out in a suitable solvent, preferably a halogenated solvent, such as, chloroform or methylene chloride.

The reaction temperature for the halogenation is expediently from –20° to 150° C. The corresponding (2-cyano-N-alkoxy)acetimidoyl halide can be obtained from the reaction mixture in an expert manner, e.g., by extraction, and, following removal of the solvent, can be used for the further conversion.

The high-temperature conversion according to the invention preferably proceeds at a temperature of from 700° to 1000° C. The reaction is usually carried out in a tubular reactor. The conversion time is generally a few seconds.

The reaction is advantageously carried out in the presence of a hydrogen donor, such as, in the presence of alkyl-substituted aromatics, preferably toluene.

Unreacted starting material can be recycled.

The malononitrile can be obtained from the reaction product, e.g., by extraction using a hydrocarbon and water, the aqueous phase being saturated with sodium chloride, and the malononitrile being re-extracted with an ether.

The (2-cyano-N-alkoxy)acetimidoyl halides of the general formula:

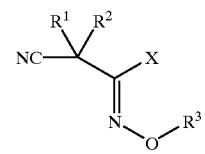

I in which $R^1$, $R^2$ and $R^3$ are as defined above, are hitherto not known in the literature and are thus also provided by the invention.

Preferred (2-cyano-N-alkoxy)acetimidoyl halides are (2-cyano-N-methoxy)acetimidoyl chloride and (2-cyano-N-ethoxy)acetimidoyl chloride.

EXAMPLE 1a

Preparation of (2-cyano-N-methoxy)acetimidoyl chloride 13.8 g (119.7 mmol) of (2-cyano-N-methoxy)acetamide was introduced at room temperature into 200 ml of chloroform. The solution was cooled to 3° C., and then 29.6 g (139 mmol) of PCl$_5$ in 70 ml of chloroform was carefully added. After the evolution of gas had subsided, 90 ml of water was carefully added at 5° C. The aqueous phase was separated off and extracted two more times with 50 ml of methylene chloride. The combined organic phases were washed with NaHCO$_3$ until neutral, dried and concentrated by evaporation. The brown residue (11.34 g) was subjected for further purification to distillation at 85° C./10 mbar. This gave 8.5 g (53 percent) of a colorless liquid which, according to $^1$H-NMR, was pure. Other data concerning the product was:

$^1$H-NMR (400 MHz, CDCl$_3$): δ=3.60 (s, 3H, CH$_2$); 4.01 (s, 3H, OCH$_3$).

$^{13}$C-NMR (400 MHz, CDCl$_3$): δ=128.3 (s); 113 (s); 63.4 (q); 26.3 (t).

EXAMPLE 1b

Preparation of (2-cyano-N-ethoxy)acetamide 13.69 g (135.3 mmol) of triethylamine was slowly added dropwise at room temperature to a solution of 12.0 g (123.0 mmol) of O-ethylhydroxylamine hydrochloride and 11.61 g (117.2 mmol) of methyl cyanoacetate in 100 ml of methanol, and the resulting mixture was stirred at room temperature for 60 hours. Although the conversion was not yet complete, the reaction mixture was evaporated to dryness. Flash column chromatography (silica gel, firstly 1:1 ethyl acetate/hexane, then ethyl acetate) of the residue produced 8.20 g (55 percent) of the title product as a white solid. Other data concerning the product was:

$^1$H-NMR (400 MHz, DMSO-d$_6$): 67 =11.2 (s, broad, NH); 2.80 (q, 2H); 3.55 (s, 2H); 1.15 (t, 3H).

$^{13}$C-NMR (400 MHz, DMSO-d$_6$): δ=159.37 (C=O); 115.53 (C≡N); 70.88 (OCH$_2$); 22.89 (CH$_2$); 13.27 (CH$_3$).

EXAMPLE 1c

Preparation of (2-cyano-N-ethoxy)acetimidoyl chloride

A suspension of 7.60 g (0.037 mmol) of phosphorus pentachloride in 30 ml of chloroform was slowly added dropwise at 3° C to a solution of 3.90 g (0.030 mol) of (2-cyano-N-ethoxy)acetamide in 70 ml of chloroform. The slightly cloudy reaction mixture was stirred at room temperature for one hour. 40 ml of H$_2$O was added dropwise with ice cooling. The phases were separated and the aqueous phase was extracted with chloroform (2×50 ml). The combined organic phases were washed with a Na$_2$CO$_3$ solution (pH 11; 2×20 ml), dried using Na$_2$SO$_4$, and the solvent was distilled off on a rotary evaporator. Kugelrohr distillation (2–4 mbar, 150° C. oven temperature) of the residue produced 3.21 g (72 percent) of the title compound as a clear, colorless oil. Other data concerning the product was:

$^1$H-NMR (400 MHz, CDCl$_3$): δ=4.25 (q, 2H); 3.60 (s, 2H); 1.32 (t, 3H).

$^{13}$C-NMR (400 MHz, CDCl$_3$): δ=127.78 (Cl—C=N); 113.46 (C≡N); 71.62 (OCH$_2$); 26.41 (CH$_2$); 14.36 (CH$_3$).

EXAMPLE 2a

Preparation of malononitrile 129 mg of (2-cyano-N-methoxy)acetimidoyl chloride was dissolved in 10 ml of toluene. This solution was injected in portions, divided into 100 μl portions, over the course of 45 minutes into a spherical vaporization flask, which was connected to a quartz pyrolysis tube (length 30 cm, internal diameter 2.5 cm and heated to 870° C.) such that the pressure, reduced by means of the vacuum pump, was maintained at 0.2 mbar. The reaction products were collected in a cold trap cooled to −196° C. Analysis of the reaction mixture using $^1$H-NMR and GC-MS indicated, as well as unreacted starting material and bibenzyl, a yield of malononitrile of 27 percent, based on the starting material used.

EXAMPLE 2b

Preparation of malononitrile 146 mg of (2-cyano-N-ethoxy)acetimidoyl chloride was dissolved in 10 ml of toluene. This solution was injected in portions, divided into 100 μl portions, over the course of 45 minutes into a spherical vaporization flask, which was connected to a quartz pyrolysis tube (length 30 cm, internal diameter 2.5 cm and heated to 870° C.) such that the pressure, reduced by means of the vacuum pump, was maintained at 0.2 mbar. The reaction products were collected in a cold trap cooled to −196° C. Analysis of the reaction mixture using $^1$H-NMR and GC-MS indicated, as well as unreacted starting material and bibenzyl, a yield of malononitrile of 25 percent, based on the starting material used.

EXAMPLE 3

Preparation and purification of malononitrile 510 mg of (2-cyano-N-methoxy)acetimidoyl chloride was dissolved in 50 ml of toluene. This solution was injected in portions, divided into 100 μl portions, over the course of 130 minutes into a spherical vaporization flask, which was connected to a quartz pyrolysis tube (length 30 cm, internal diameter 2.5 cm and heated to 870° C.) such that the pressure, reduced by means of the vacuum pump, was maintained at 0.3 mbar. The reaction products were collected in a cold trap cooled to −196° C. The contents of the cold trap were transferred to a separating funnel, and the cold trap was rinsed with 50 ml of hexane and twice with 40 ml of water. The combined solutions were extracted with water (a total of 150 ml) and the phases separated. 52 g of sodium chloride was added to the aqueous phase, which was then extracted by shaking three times with diethyl ether (a total of 700 ml). The etheric phase was dried using MgSO$_4$, and the solvent was removed under reduced pressure. According to $^1$H-NMR, the residue consisted of 95 percent of malononitrile and 5 percent of the starting material. The yield was 26 percent, based on the starting material used.

The following experiments were carried out as in Example 2 but with different quartz tube temperatures.

| | Temperature ° C. | Yield in % of malononitrile | Starting Material | Bibenzyl |
|---|---|---|---|---|
| 4 | 570° | 2 | 74 | 5 |
| 5 | 670° | 13 | 26 | 9 |
| 6 | 770° | 15 | 19 | 15 |
| 7 | 820° | 18 | 9 | 17 |
| 8 | 870° | 27 | 11 | 29 |
| 9 | 920° | 23 | 11 | 20 |
| 10 | 970° | 23 | 7 | 25 |

What is claimed is:

1. A process for the preparation of malononitrile, characterized in that a (2-cyano -N-alkoxy )acetimidoyl halide of the formula:

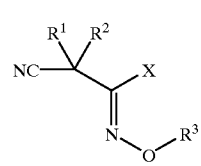

I in which R$^1$ and R$^2$ are identical or different and are hydrogen or alkyl, R$^3$ is alkyl, cycloalkyl, aryl, arylalkyl or a group:

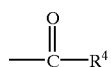

in which $R^4$ is an alkyl, aryl or arylalkyl group, and X is a halogen atom, is converted into malononitrile by a temperature of from 500° to 1000° C.

2. The process according to claim 1, wherein the conversion is carried out at a temperature of 700° to 1000° C.

3. The process according to claim 2, wherein the (2-cyano-N-alkoxy)acetimidoyl halide of the formula I is prepared by halogenation of a (2-cyano-N-alkoxy)acetamide of the formula:

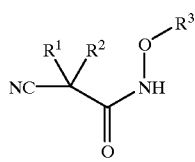

II in which $R^1$ is as defined above.

4. The process according to claim 3, wherein the halogenation is a chlorination and is carried out using phosphorus pentachloride, phosphene, phosphorus oxychloride or tetrachloromethane in conjunction with triphenylphosphine.

5. The process according to claim 4, wherein the halogenation is carried out in the presence of a halogenated solvent at a reaction temperature of from −20° to 150° C.

6. The process according to claim 3, wherein the halogenation is carried out in the presence of a halogenated solvent at a reaction temperature of from −20° to 150° C.

7. The process according to claim 1, wherein the (2-cyano-N-alkoxy)acetimidoyl halide of the formula I is prepared by halogenation of a (2-cyano-N-alkoxy)acetamide of the formula:

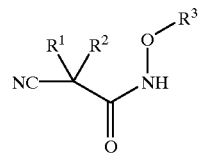

II in which $R^1$ is as defined above.

8. (2-Cyano-N-alkoxy)acetimidoyl halide of the formula:

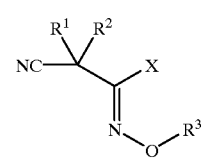

I in which $R^1$ and $R^2$ are identical or different and are hydrogen or alkyl, $R^3$ is alkyl, cycloalkyl, aryl, arylalkyl or a group:

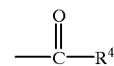

in which $R^4$ is an alkyl, aryl or arylalkyl group, and X is a halogen atom.

* * * * *